United States Patent [19]

Kumar et al.

[11] Patent Number: 6,127,405
[45] Date of Patent: Oct. 3, 2000

[54] METHOD FOR THE USE OF ALPHA ARTEETHER AS AN ANTI-BACTERIAL AND ANTI-FUNGAL AGENT

[75] Inventors: Sushil Kumar; Suman Preet Singh Khanuja; Tiruppadiripuliyur Ranganathan Santha Kumar; Dharam Chand Jain; Suchi Srivastava; Asish Kumar Bhattacharya; Dharmendra Saikia; Ajit Kumar Shasany; Mahendra Pandurang Darokar; Ram Prakash Sharma, all of Lucknow, India

[73] Assignee: Council of Scientific and Industrial Research, New Delhi, India

[21] Appl. No.: 09/179,204

[22] Filed: Oct. 27, 1998

[30] Foreign Application Priority Data

Jul. 10, 1998 [IN] India ............... 1967/DEL/98

[51] Int. Cl.$^7$ .................................................. A61K 31/335
[52] U.S. Cl. .............................................................. 514/450
[58] Field of Search ............................................. 514/450

[56] References Cited

U.S. PATENT DOCUMENTS 5,057,501  10/1991  Thornfeldt ................................ 514/53

*Primary Examiner*—Kevin E. Weddington
*Attorney, Agent, or Firm*—Ladas & Parry

[57] ABSTRACT

The present invention relates to use α-arteether as a antibacterial agent, preferably for gyr mutant bacteria which are resistant to quinolone drugs and can be used as therapeutic agents for treating drug resistant bacterial infections, and also as a antifungal agent.

6 Claims, No Drawings

METHOD FOR THE USE OF ALPHA ARTEETHER AS AN ANTI-BACTERIAL AND ANTI-FUNGAL AGENT

FIELD OF THE INVENTION

The present invention relates to a method for the use of α arteether as a fourth generation anti-bacterial and anti-fungal drug.

BACKGROUND OF INVENTION

The plant *Artemisia annua* (family: Asteraceae) produces a sesquiterpenoid lactone endoperoxide named artemisinin which is a promising antimalarial drug effective against *Plasmodium falciparum, Plasmodium vivax* at nanomolar concentration. Artemisinins are active against *Schistosoma mansoni* and *S. japonicum* in-vitro and in-vivo in experiments in animals. These schistosomes, like malarial parasites, degrade haemoglobin and produce hemozoin. These compounds are also active against *Leishmania major, Toxoplasma gondii* and *Pnenmocystic carinii* in-vitro and against *P. carinii* in-vivo. Artemisinins have immunosuppressive activity and also potential anticancer activity. For these activities, the doses of artemisinin required are substantially higher than the dose for antimalarial activities. According to Meshnick et at., (1996) (Microbiological Reviews 6:301–315) the antimalarial endoperoxides including artemisinin, dihydroartemisinin and arteethers, are not likely to be useful for other therapeutic purposes except against malarial parasites.

Fluoroquinolones, such as ciprofloxacin and ofloxacin are currently used against multi-drug resistant tuberculosis as alternatives to the first line agents such as isoniazid, streptomycin and rifampicin (Drlica et al., 1995; In. W. Rom and S. Garay (ed), Tuberculosis. Little, Brown & Co., Boston). However, M. tuberculosis frequently tends to acquire resistance to the quinolones, limiting their clinical usefulness (Tsukamura et al., 1985, Am, Rev. Respir. Dis. 131:352–56). Therefore, newer drugs which are effective against quinolone resistant pathogenic bacteria need to be evolved. It is also worthwhile to note that mycobacteria and *E. coli* respond to quinolone treatment in a similar fashion, justifying the extrapolation of the concepts developed with *E. coli* to mycobacteria. Both these bacteria develop resistance to quinolone drugs by virtue of point mutations in a short stretch of nucleotides known as the quinolone determining region within the gyrA gene encoding DNA gyrase subunit A (Cambau et al., 1994, Journal of Infactious Diseases 170: 479–83). Mycobacterium tuberculosis infects ten million people and kills three million each year making it the greatest cause of mortality by a single infectious agent worldwide. Quinolones have been shown to inhibit DNA gyrase activity such supercoiling and in turn DNA replication. Several investigators have shown that point mutations in gyrA gene occurring in very small region between 0–400 nucleotides of the gene are responsible for quinolone resistance acquired by different strains of *E. coli* selected either in-vitro or in vivo. The similarity of action of fluoroquinolones in Mycobacterium sp. and *Haemophilus influenzae* and the subsequent resistance mechanisms that have developed due to mutations in gyrA gene are related to *E. coli*. So the mechanism of quinolone resistance are similar between *E. coli*, Mycobacteria and *H. influenzae* (Georgiou et al., 1996, *Antimicrobial Agents and Chemotherapy* 40: 1741–1744 Cambau et al., 1994, *The Journal of Infectious Diseases* 170: 479–483).

During the past decade, bacteria that cause human diseases have been reported to be fast developing genetic resistance to many of the antibiotics commonly used for treatment (Witte 1998, *Science* 279: 996–998). All of the pathogens usually reported in hospitals including mycobacteria, pneumococci and enterobacteriaceae are known to develop drug resistance. Although, the emergence of drug resistance is a serious health concern, the appearance of multi-drug resistant strains of Mycobacterium tuberculosis (MDR-TB) is more disturbing since few drugs are effective against tuberculosis (Bloom et al.,1992, *Science* 257: 1055–1064; Heym et al., 1994, *Lancet* 344: 293–298). Such MDR-TB has resulted in fatal outbreaks in many countries, including the United States (Snider et al., 1992, *New England Journal of Medicine* 326: 703). Strains of MDR-TB which are resistant to as many as seven drugs have already been reported (Frieden et al., 1993, *New England Journal of Medicine* 328: 521). Development of bacterial resistance to drugs costs not only money but also human lives. Resistant infections are associated with increased morbidity, prolonged periods during which individuals are infectious and greater opportunity for the spread of infections to other individuals. The available antibiotics at present are usually of fungal origin against which a wide spectrum of drug resistance genes have already evolved.

Because of the omnipresence of the bacterial diversity in the biosphere, plants have always been exposed to bacterial infections. At the same time, plants exhibit natural resistance to bacterial attack and therefore possess compounds effective against pathogenic bacteria which have developed resistance to various drugs. Such plant compounds are classified as fourth generation antibiotics, useful in treating infectious diseases.

As mentioned earlier, artemisinin is effective against malaria. Although artemisinin rapidly suppresses the activity of parasites like plasmodium vivax and *P. falciparum*, problems with high rate of recrudescence (>10% recrudescence infections), short half life persist. Hence, there is a need to develop new drugs against quinolone resistant pathogenic bacteria. It is a known fact that clinically used antibacterial broad spectrum compounds such as quinolones which exhibit DNA gyrase activity of mycobacterium sp. (causing tuberculosis) and Haemophilus sp. (causing tuberculosis) and *Haemophilus influenzae* are gradually becoming ineffective due to the occurrence of mutatious in gyrase genes and their natural selection under continuous use of such drug.

The Applicants, during their research screened a number of semisynthetic artemisinin related compounds to check the anti-bacterial and anti-fungal activity. The Applicants studied the nature of α and β arteether, synthesised from dihydroartemisinin by etherification with ethanol. These compounds were developed as antimalarial drugs by Central Drug Research Institute (CDRI), Lucknow, India and Central Institute of Medicinal & Aromatic Plants (CIMAP), Lucknow, India, after phase II clinical trial. The absolute stereochemistry of arteethers at C-12 were also determined and it was found to be 2–3 times more potent than artemisinin. The Applicants during their research, came across α-arteether and β-arteether out of which α-arteether was found to inhibit the growth of *E-coli* strains defective in DNA-gyrase enzyme. The applicants observed that DNA gyrase mutants were sensitive to α-arteether whereas the wild type of *E-coli* having intact DNA gyrase genes were not sensitive to said α-arteethers. In fact, the isomer of this compound, β-arteether, does not exhibit this activity.

As such, the Applicants found a novel property of α-arteether as being effective against the gyr mutant strains of *E. coli* but ineffective against wild type strains. This will help to generate next generation antibiotics to kill the infectious bacteria which have already developed resistance to quinolones and fluoroquinolones. Hence, the Applicants also tested the efficacy of the compounds against fungi and found that it inhibits fungal growth due to its antifungal activity. The uses of artemisinin endoperoxide as an antimalarial drug and the potential use of the compound as antiprotozoan is well cited in the literature. However, the novel use of αarteether, a semisynthetic endoperoxide as a drug for bacterial infections caused by quinolone resistant bacteria and its use as an antifungal agent is novel and has not been reported earlier.

It is an object of the present invention to use α-arteether as a drug for gyr mutant bacteria which are resistant to quinolone drugs, and can be used as therapeutic agents for treating drug resistant bacterial infections.

It is yet another object of the invention to identify the antifungal function of an agent, the novel use of which was not known previously.

In accordance with the above objects, the present invention provides a method for treating bacterial or fungal infections in animals using α-arteether.

DETAILED DESCRIPTION OF THE INVENTION

In this invention, the Applicants have found through bioactivity assays that the plant based compound α-arteether has a unique property of killing drug resistant bacteria which have developed the genetic resistance against quinolone drugs. The compound α-arteether is obtained by etherification of artemisinin (a sesquiterpenoid lactone endoperoxide) produced by the plant *Artemisia annua*. The compound α-arteether in our experiments was demonstrated to be killing nalidixic acid resistant strains of *Escherichia coli* and *Mycobacterium smegmatis*. In such strains the mutation in the gyrase gene had conferred the resistance against nalidixic acid and other quinolones. Interestingly, even the β-isomer of arteether lacked this activity. In addition, the compound also showed antifungal activity in the bioassays. The compound being of plant origin and already in use as a component of antimalarial drug in form of mixture of α- and β-arteethers is safe having no toxicity on human beings. Due to its property of killing the bacteria which have developed resistance against advanced generation drugs (quinolones and fluoroquinolones) and its fungus inhibition properties, the use of α-arteether as the fourth generation antibacterial and antifungal drug has been revealed in the invention.

It is a known fact that quinolones and fluoroquinolones are a group of the most potent broad spectrum antibacterial agents currently used for various kinds of infections. The Applicants have tried to find out whether it is possible to define the molecular target for α-arteether as an advance generation drug because DNA gyrase isolated from quinolone resistant strains are known to be resistant to quinolones. In fact, the mechanism of resistance to quinolones and fluoroquinolones is strikingly similar among *E.coli*, *Mycobacterium smegmatis*, *Mycobacterium tuberculosis*, *Bacillus subtilis* and *Haemophilus influenzae* and Salmonella typhimurium is due to mutations in the gyrA gene, indicating that the mechanism of resistance to quinolones are similar among these bacteria (Cambau et al., 1994, *The Journal of Infectious Disease* 170: 479–483; Ruiz et al., 1997, *Journal of Medical Microbiology* 46: 623–628). Therefore, nalidixic acid resistant mutants of *Mycobacterium smegmatis* (ATCC 14468) were isolated and found that these mutants were also sensitive to α-arteether whereas the wild type was insensitive. This proves that quinolone resistant Mycobacterium sp. are also sensitive to a α-arteether as is in the case of *E. coil*.

The search for novel drugs with unique mode of action is usually conducted using mechanism based screens. The use of microbiological assays for the detection of molecules biologically active in eukaryotes has been described on several occasions. Such screens have the advantage of speed and simplicity. It facilitates the selective detection of agents which inhibit specific function. The Applicants have used this logic while screening the products from natural sources against mutant bacterial strains.

The Applicants conducted experiments to detect the biological activity of α-arteether against strains of *Escherichia coli* and found that among several strains only one commercially available *E. coli* strain DH5α- (Source: Life Technologies Inc., Gaithensburg, Md. USA) had unique drug sensitivity property. This strain carrying a well defined gyrA 96 mutation was found to be sensitive to α-arteether. It also showed resistance to nalidixic acid. The other wild type strains which were nalidixic acid sensitive invariably showed resistance to α-arteether. Therefore, to ascertain whether the gyrA mutation is responsible for α-arteether sensitivity, other commercially available *E. coli* strains such as XL1 (Source: Stratagene GmbH, Heidelberg, FRG) and JM-107 (Source: New England Biolabs Inc., Beverly, Mass. USA) carrying gyrA mutation were also tested. And these strains were also found to be α-arteether sensitive.

One commonly used wild type laboratory stain of *E. coil*, CA8000 (Source: J. Beckwith, Harvard Medical School, Massachusettes, USA; S. Kumar, Central Institute of Medicinal & Aromatic Plants, Lucknow; India -226015) is sensitive to nalidixic acid. This strain was found to be inherently resistant to α-arteether. Therefore nalidixic acid (Nal) resistant mutant derivatives of CA8000 were isolated. These Nal resistant CA 8000 mutants were also found to be sensitive to α-arteether. It is a well known fact that the nalidixic acid and coumermycin resistant *E. coli* cells carry mutations in the gyrA and gryB genes (Gellert et al., Proc. Natl. Acad. Sci. USA, 73:4474–78; Gellert et al., Proc Natl. Acad. Sci. USA, 74: 477–2776; Sugino et. Al., Proc. Natl. Acad. Sci. USA 74:4767–4771). For further substantiating the gyr (−) and α-arteether resistance relationship in *E. coli* MTCC 482 (Commercial Source: Microbial Type Culture Collection, Institute of Microbial Technology, Chandigarh; India-160036) which is defective in gyrB locus were tested for α-arteether sensitivity. Interestingly, this strain was also α-arteether sensitive. Thus, it became obvious that stains of *E. coli* defective in DNA gyrase enzyme were involved in regulating the DNA supercoiling, and were specifically inhibited by α-arteether. On the other hand all the above gyr mutant strains did not show sensitivity to the β-isomer of arteether. As a further supporting experimental evidence, α-arteether resistant DH 5α cells were isolated which have simultaneously reverted to nalidixic acid sensitive phenotype. Thus, resistance to one of the above compounds would render the *E. coli* cells sensitive to the other compound.

To define precisely the involvement of gyr genes in the α-arteether sensitivity, two recombinant clones called pMK 90 and pMK 47 containing wild type gyrA and gyrB genes respectively were utilized in trans-complementation assays (Mizuuchi et al., 1984, The Journal of Biological Chemistry 259:9199–9201). For this purpose, the plasmid clones were introduced into the *E. coli* nalidixic acid resistant gyr mutant strains. The resulting transformants were now nalidixic acid sensitive and α-arteether resistant. This supported the observation that DNA gyrase of *E. coli* is involved in α-arteether sensitivity.

Accordingly, the invention provides a method of using α-arteether as an antibacterial and antifungal agent which comprises:

(a) Isolating quinolone resistant *E. coli* bacteria by mutagenesis, (b) Screening of quinolone resistant *E. coli* bacteria against artemisinin related endoperoxides, (c) Identifying the activity of α-arteether against quinolone resistant *E. coli* bacteria in disk diffussion assays, (d) Selection of α-arteether resistant *E. coli* bacteria, (e) Screening of α-arteether resistant *E. coli* bacteria against nalidixic acid, (f) Identifying the sensitivity of α-arteether resistant bacteria to nalidixic acid by validating the phenotypic properties the said property being α-arteether sensitive or nalidixic acid resistance or vice-versa, (g) Introduction of wild type gyr A gyr B genes into quinolone resistant *E. coli* bacteria called transformants, (h) Screening of transformants against α-arteether by standard methods, (i) Identifying the resistance of transformants to α-arteether activity, (j) Identifying the specific inhibition of quinolone resistant *E. coli* bacteria by α-arteether, (k) Isolating quinolone resistant *Mycobacterium smegmatis* by mutagenesis, (l) Identifying the specific inhibiting of quinolone resistant *Mycobacterium smegmatis* by α-arteether, (m) Screening of fungal cultures against artemisinin related endoperoxides by broth dilution method, and (n) Measuring the minimal inhibitory concentration demonstrating that α-arteether can be used as an antifungal agent.

The concentration of nalidixic acid used for the identification of quinolone resistant *E. coli* bacteria ranges between 10–20 μg/ml and the screening of quinolone resistant *E. coli* bacteria against artemisinin endoperoxides is done by disk diffusion method at a moderate concentration ranging from 80–320 μg/disc. The artemisinin endoperoxides used for screening and activity comparison are selected from the group comprising artemisinin, dihydroartemisinin, arteannuin, α-arteether and β-arteether.

The activity of α-arteether against quinolones is identified by the formation of halo zone of growth inhibition ranging from 13 to 20 mm in diameter. The minimal inhibitory concentration of α-arteether against quinolone resistant bacteria determined by broth dilution method ranges between 100–400 μg/ml of α-arteether. The halo zone of inhibition of fungal strains in the presence of α-arteether at a concentration of 320 μg/disc ranges between 15 to 20 mm. in diameter. Wild type gyrA and gyrB genes are introduced into quinolone resistant bacteria. Nalidixic acid sensitive phenotype of the transformants are identified by poison agar method which is done at a concentration ranging between 10 to 50 μg/ml. The drug resistant bacteria include *E. coli* and the drugs include nalidixic acid and its analogues fluoroquinolones, and such drug resistant bacteria also include other infectious bacteria such as Mycobacterium spp. and the drugs include nalidixic acid and its analogs thereof such as fluoroquinolones. In one embodiment of the invention involves differentiating α-arteether from its isomer β-arteether as well as other artemisinin endoperoxides.

In another embodiment of the invention, the method of using α-arteether as an antibacterial and antifungal agent includes:

(a) Identifying the quinolone resistant *E. coli* bacteria from the mutagenized stock culture at a concentration of nalidixic acid ranging from 10–20 μg/ml, (b) Screening of quinolone resistant *E. coli* bacteria against artemisinin endoperoxides by disc diffusion method at a moderate concentration ranging from 80–320 μg per disc, (c) Identifying the activity of α-arteether against quinolone resistant *E. coli* bacteria by the formation of halo zone of growth inhibition ranging from 13 to 20 mm in diameter (moderate to high sensitivity), (d) Identifying the α-arteether resistant *E. coli* from a mutagenized population of quinolone resistant cells in the presence of α-arteether at a concentration of more than 1000 μg/ml, (e) Identifying the sensitivity of α-arteether resistant *E. coli* bacteria to nalidixic acid at concentration of 20 g/ml validating the interchangeability of both the phenotypes, (f) Introduction of wild type gyr A gyr B genes into quinolone resistant *E. coli* bacteria called transformants, (g) Identifying the nalidixic acid sensitive phenotype of the transformants by poison agar method which is done at a concentration ranging between 10–50 μg/ml of nalidixic acid, (h) Identifying the resistance phenotype of the transformants of α-arteether by observing the reduction in halo size of inhibition from 16 mm to 11 mm at a concentration of 320 μg/disc, (i) Identifying the specific inhibition gyr-mutants or quinolone resistant *E. coli* bacteria by α-arteether n at a concentration ranging from 80–320 μg/disc, (j) Identifying the specific inhibiting of gyr-mutants or quinolone resistant *Mycobacterium smegmatis* by α-arteether at a concentration ranging from 80–320 μg/disc, (k) A method of screening of fungal cultures against artemisinin related endoperoxides by broth dilution method at a concentration of 25–4000 μg/ml, and (l) The minimal inhibitory concentration of 1000–2000 μg/ml of α-arteether against some fungal strains.

The invention is further illustrated by the following examples which should not be construed to limit the scope of the invention.

EXAMPLES

1. As a starting step to determine the relationship, if any, between the α-arteether sensitivity and various essential and general functions/genes the screen of (mechanism based) the modified and wild type strains of *E. coli* were used for bioassays. This was performed by single disc diffusion assay as per Bauer et al., 1966, (*American Journal of Clinical Pathology* 45: 493–496) with slight modifications. The discs were prepared (5 mm diameter made of Whatman #3 filter paper) by impregnating 8 μl of test compound and placing them on pre-inoculated agar surface. A disc containing only the solvent was used as the control. As evident from this example the results indicate that only one strain of *E. coli* DH5α which carries a gyrA 96 mutation was susceptible to α-arteether. Of the other strains of *E. coli* carrying different types of mutants defective in recombination pathway, aromatic amino acids biosynthesis pathway and cyclic AMP synthesis were not susceptible to α arteether (Table-1). This example provided the first indication that the α arteether specifically kills DNA gyrase defective *E. coli* cells.

TABLE 1

| | | | Zone of inhibition (mm) α-arteether concentration (µg/disc) | |
|---|---|---|---|---|
| Strains | Genotype | Source | 160 | 320 |
| HB 101 | pro, leu, rec A, rpsL | Life Technologies MD, USA | — | — |
| ER 1648 | F-fhu, trp, supE, mcrA, | New England Biolabs MA, USA | — | — |
| CA8000 | thi, Hfr | S. Kumar, Central Institute of Medicinal % Aromatic Plants Lucknow, India. | — | — |
| DH 5α | end A, rec A, gyr A, relA, hsd R, Δlac Z | Life Technologies MD, USA | 13 | 16 |

2. The observations of example-1 formed the basis of our hypothesis that α-arteether sensitivity is related to the form or conformation of DNA gyrase which is involved in DNA replication. Supportive experiments were carried out in this example to substantiate or reject the hypothesis. The bioassays were carried out to test whether $E.$ $coli$ strains other than DH5α carrying gyrA and gyrB mutations were also susceptible to α arteether. The strains XL-1 and JM-107 in this example carried known gyr mutations. The experiments for α arteether activity constituted disc diffusion assay as in example 1. The results clearly demonstrated that the strains XL-1 and JM-107 carrying gyrA mutations as well as strain MTCC-482 carrying gyrB mutation were also susceptible to α-arteether at the same concentration (Table-2). This example accepted our postulated hypothesis that gyr mutations in any $E.$ $coli$ background confer susceptibility to α-arteether.

TABLE 2

| | | Relative zone of Inhibition (RZI)* α-arteether concentration (µg/disc) | | |
|---|---|---|---|---|
| Strains | Mutations located | 80 | 160 | 320 |
| DH 5α | gyr A 96 | 2.2 | 2.6 | 3.2 |
| XL-1 | gyr A(-) | 2.2 | 2.2 | 2.6 |
| JM 107 | gyr A(-) | 2.4 | 2.6 | 2.8 |
| MTCC 482 | gyr B(-) | 2.2 | 2.6 | 2.8 |
| CA8000 | wild type | 1.0 | 1.0 | 1.0 |

Note:

*RZI is calculated as = $\dfrac{\text{Diameter of the zone of inhibition (B)}}{\text{Diameter of the filter paper disc (A)}}$

*RZI is 1.0 indicates no inhibition.

3. Our subsequent experiments have been devised to critically examine the arguments that might arise in the light of the above findings. We first argued that the $E.$ $coli$ strain DH5α is auxotrophic in nature carrying multiple mutations which are not linked to DNA gyrase activity. We wanted to eliminate the possibility that any of these mutations might influence arteether sensitivity pattern. To test this arguments we isolated gyrA mutants in $E.$ $coli$ strain CA8000 which is an otherwise wild type strain. GyrA mutants were selected as nalidixic acid resistant (20 µg/ml) cells from among the population of EMS (Ethylmethane sulphonate) mutagenized cells (Miller,1972; *Experiments with Molecular Genetics* page 466, Cold Spring Harbor Laboratory Press, New York). EMS is a chemical which is widely used to create mutations in the bacterial genome by alkylation of nitrogen bases in the deoxy-ribonucleic acids (DNA). The gyrA genotype of these mutants were confirmed by trans complementation assay using gyrA (pMK 90) and gyrB (pMK 47) clones; described in the later examples. Five such gyrA nalidixic acid resistant mutants of CA8000 named as Nal 01,02,03,06 and 07 were isolated and found to be α-arteether sensitive; whereas the wild type CA8000 was resistant (Table-3).

4. As a means of further confirmation on this argument, mutants of DH5 α cells resistant to α-arteether at the rate of 1 mg/ml were isolated by NG (N-Methyl-N'-nitro-N-Nitrosoguanidine) mutagenesis (J. H. Miller, 1972, Experiments in Molecular Genetics, page: 125–129, Cold Spring Harbor Laboratory, NY, USA). Since, the gyrA locus is involved in both α-arteether sensitivity and nalidixic acid resistance phenotype we expected simulation reversion from nalidixic acid resistance to sensitive phenotype. It was indeed true as two such α-arteether resistant isolated cells were also Nal sensitive. The above two examples unequivocally proved that sensitivity to α-arteether in the $E.coli$ strains described previously is determined by defective DNA gyrase enzyme rather than the multiple mutations identified or otherwise.

TABLE 3

| Strains | Relative zone of inhibition at 320 µg/disc of α arteether concentration |
|---|---|
| CA8000 (wild type) | 1.00 (–) |
| NAL 01 | 2.60 (13) |
| NAL 02 | 2.40 (12) |
| NAL 03 | 3.26 (16) |
| NAL 06 | 2.80 (14) |
| NAL 07 | 3.20 (16) |

Values in parentheses indicate actual diameter of the zone of inhibition (mm)
All the mutants (NAL 01–07) were selected at nalidixic acid 20 µg/ml.
Relative Zone of Inhibition measured as in example-2

Introduction wild type gyrase genes into gyr $E.$ $coli$ cells would transform the cells to come Gyr+ (nalidixic acid sensitive) and α-arteether resistant simultaneously. Hence, complementation tests were performed using plasmids pMK90 and pMK47 harboring cloned gyrA and gyrB genes respectively in thermo-inducible λ col E I cloning vector pKC16 (Source: Dr. H. K. Das, JNU; New Delhi). Hence, culture conditions were modified when assaying for drug sensitivity using these plasmids. After overnight growth, the cultures were shifted to 42° C. for 15 minutes and then allowed to grow further at 37° C. for 3 to 4 hours, before performing disk diffusion assays. Both the plasmids pMK 90 and pMK47 were introduced into *E. coli* gyrA mutant strains XL-1, JM-107 and DH5α. The transformed cells were tested for the complementation of nalidixic acid sensitivity by poison agar method wherein, the said compound nalidixic acid was directly mixed into the growth medium at a concentration ranging between 10–50 μg/ml and the culture grown on the medium. The transformants were also tested for α-arteether resistant phenotype in the presence of ampicillin. It was found that the cloned gyrase genes could complement both these phenotypes (Table-4). This suggests that mutation in the gyrA locus is responsible for both nalidixic acid resistance as well as α-arteether sensitivity and the *E. coli* strains defective in DNA supercoiling are sensitive to α-arteether.

TABLE 4

| | Sensitivity measured as zone of inhibition (mm) | | | | |
|---|---|---|---|---|---|
| Strains/ | Resistance to Nalidixic acid (μg/ml) | | | Concentration of α arteether (μg/disc) | |
| Clones | 10 | 25 | 50 | 160 | 320 |
| DH 5 α | ++ | ++ | ++ | 14 | 16 |
| DH 5 α (pMK 90) | + | -- | -- | 11 | 11.5 |
| DH 5 α (pMK 47) | ++ | ++ | + | 14 | 15 |
| XL-1 | ++ | ++ | + | 13 | 15 |
| XL-1 (pMK 90) | -- | -- | -- | 9 | 9.5 |
| XL-1 (pMK 47) | ++ | ++ | + | 12 | 13 |
| JM-107 | ++ | ++ | ++ | 11 | 13 |
| JM-107 (pMK 90) | + | -- | -- | 9 | 10 |
| JM-107 (pMK 47) | ++ | ++ | ++ | 12 | 14 |

*Observation are averages of at least six independent transformants in each of the strain.
Sensitivity estimated in the presence of ampicillin.
++, good growth --, no growth +, moderate growth 6. The observations made in the previous examples, unequivocally proved that gyr-property is responsible for sensitivity to α-arteether in *E. coli*. It is an established fact that the resistance to nalidixic acid as well as other quinolone drugs in many pathogenic bacteria such as *Mycobacterium tuberculosis*, Campylobacter sp., *Haemophilus influenzae* are also due to mutations in the gyrA gene, indicating that the mechanism of resistance to quinolones are similar among these bacteria. Therefore, we isolated nalidixic acid resistant mutants of *Mycobacterium smegmatis* (ATCC 14468) through UV induced mutagenesis by growing the mutagenized cells in the presence of nalidixic acid @ 50 μg/ml. and found by disc diffusion assay that these mutants were also sensitive to α-arteether whereas the wild type strain was insensitive (Table-5). This proves that quinolone resistant Mycobacterium sp. are also sensitive to α-arteether as is in the case of *E coli*.

TABLE 5

| | | Relative zone of Inhibition (RZI)* α arteether concentration (μg/disc) | | |
|---|---|---|---|---|
| Strains | Phenotype | 80 | 160 | 320 |
| *Mycobacterium smegmatis* (ATCC 14468) | wild type (Nal-S) | 1.0 | 1.0 | 1.0 |
| Mutant-1 | Nal-R | 2.0 | 3.0 | 4.2 |
| Mutant-2 | Nal-R | 2.0 | 3.0 | 4.0 |

RZI was calculated as in example-2
RZI of 1.0 indicates absence of zone of inhibition.
Nal-R = Nalidixic acid resistant; Nal-S = Nalidixic acid sensitive.

7. In order to test whether α-arteether can be used as antifungal agent, agar diffusion assays was done (Wannissorn et al. 1996, *Phytotherapy Research* 10:551–554). α-arteether was dissolved in dichloromethane:dimethyl sulfoxide (1:1) solvent to obtain stock solution and applied on to filter paper discs (diameter 5 mm, Whatman #3) at the rate of 8 μl /disc. The discs were then transferred on to the surface of the seeded agar plate and gently pressed down to ensure contact. The plates were incubated at 28° C. for 48 h. The inhibition zone was measured as the diameter of the clear halo zone around each disc.

TABLE 6

| Strain | Genotype | Minimal inhibitory concentration of α-arteether |
|---|---|---|
| *Saccharomyces cerevisiae* | | |
| EG-1-103 | leu2 trp1 Ura3 | 2.0 |
| ABC-287 | Ura3 leu2Δ1 his3Δ200 pep4ΔHis3 Prb1 Δ1.6R can1 GAL lys2-801 | — |
| ABC-288 | Ura3 leu2Δ1 his3Δ200 pep4Δ His3 Prb1Δ1.6R can1 GAL lys2-801 trp1 sts1Δ TRP1 | — |
| F-400 | gal7 lys2 tyr1 leu2 his4 thr4 MAL2 trp1 ade6 arg4 ura4 | 1.0 |
| JN-284 | MATa isel1 Ura 3-52 leu2 (3,112) his7-2 | — |

Minimum concentration (mg/ml) of test substance in the stock solution required to produce a halo zone of atleast 7 mm diameter (including the paper disc) when 8 μl/disc was applied.

The MIC is measured as the minimum concentration of test substance (mg/ml) in the stock solution required to form a halo zone of atleast 7 mm diameter, including that of the paper disc. The results indicated (Table-6) that α-arteether possessed the antifungal activity.

8. In each of the above working examples α-arteether was prepared from artemisinin, isolated from *Artemisia annua* plant. For the preparation of dihydroartemisinin from artemisinin, 150 mg of $NaBO_4$ was added to a cooled and stirred solution of 100 mg of artemisinin in 5 ml of dry methanol, over a period of 30 min. After completion of reaction, reaction mixture was diluted with water and extracted with $CH_2Cl_2$ (3×100 ml). The organic extract was washed with water, dried over $Na_2SO_4$ and evaporated to furnish the dihydroartemisinin in 85% yield. For the preparation of arteether from dihydroartemisinin, 0.5 ml of chlorotrimethyl silain (CTMS) was added to a solution of 100 mg of dihydroartemisinin in 2 ml of dry benzene and 3 ml of ethanol and the reaction mixture was stirred at room temperature. After completion of the reaction, the reaction mixture was diluted with water and extracted with $CH_2Cl_2$ (3×φml). The organic layer was washed with water dried over $Na_2SO_4$ and evaporated to furnish a residue which on purification by preparatory TLC (ethylacetate- hexane 9:1) afforded 65 mg of β arteether as solid (mp. 80–82° C.) and 25 mg of (α arteether as an oil. Both the compounds were identified on the basis of spectral data. α and β arteether were dissolved in dichloromethane and dimethyl sulfoxide in 1:1 ratio for biological assay.

The example herein described and illustrated both references indicate a new property of α-arteether; is it advantageous than the existing drugs due to the fact that it can specifically kill quinolone resistant pathogenic (infectious) bacteria and therefore can be useful in treating quinolone resistant bacterial infections. Moreover the said compound is a semi-synthetic derivative of artemisinin derived by a simple etherification step. Artemisinin being a natural compound isolated from a plant *Artemisia annua* is available easily from natural sources.

What is claimed is:

1. A method for inhibiting the growth of a bacterial strain, wherein the bacterial strain is resistant to a quinolone drug by virtue of a mutation in a gyrase gene thereof, the method comprising contacting or causing contact of the strain with α-arteether in an amount effective to inhibit the growth.

2. A method according to claim 1, wherein the bacterial strain is a strain of *E. coli* or a strain of mycobacteria.

3. A method for treating an infection in an animal caused by a bacterial strain, wherein the bacterial strain is resistant to a quinolone drug by virtue of a defect in a gyrase enzyme, said method comprising administering to the animal an amount of α-arteether effective to kill the bacterial strain.

4. A method according to claim 3, wherein the bacterial strain is a strain of *E. coli* or a strain of mycobacteria.

5. A method for treating an infection in an animal caused by a fungus, said method comprising administering to the animal α-arteether in an amount effective to kill the fungus.

6. A method for screening bacteria, comprising
   (a) contacting the bacteria with a quinolone and isolating bacteria that are resistant to the quinolone; and
   (b) contacting the quinolone resistant bacteria isolated in step (a) with α-arteether to determine their susceptibility to the α-arteether.

* * * * *